United States Patent [19]

Kuroda et al.

[11] Patent Number: 4,861,692
[45] Date of Patent: Aug. 29, 1989

[54] ELECTROPHOTOGRAPHIC PHOTOSENSITIVE MATERIAL CONTAINING THIOPHENE COMPOUND

[75] Inventors: Masami Kuroda; Yoichi Nakamura; Noboru Furusho, all of Kanagawa, Japan

[73] Assignee: Fuji Electric Company, Ltd., Kanagawa, Japan

[21] Appl. No.: 136,661

[22] Filed: Dec. 22, 1987

[30] Foreign Application Priority Data

| Dec. 22, 1986 [JP] | Japan | 61-305633 |
|---|---|---|
| Dec. 22, 1986 [JP] | Japan | 61-305653 |
| Dec. 23, 1986 [JP] | Japan | 61-306874 |
| Dec. 23, 1986 [JP] | Japan | 61-306876 |
| Dec. 23, 1986 [JP] | Japan | 61-306880 |

[51] Int. Cl.⁴ .............................................. G03G 5/14
[52] U.S. Cl. ........................................ 430/59; 430/73
[58] Field of Search ................ 430/70, 71, 72, 73, 430/76, 77, 59

[56] References Cited

U.S. PATENT DOCUMENTS

| 3,242,188 | 3/1966 | Siegrist et al. | 430/77 |
|---|---|---|---|
| 4,554,231 | 11/1983 | Ishikawa et al. | 430/77 |

*Primary Examiner*—John L. Goodrow
*Attorney, Agent, or Firm*—Sughrue, Mion, Zinn, Macpeak & Seas

[57] ABSTRACT

An electrophotographic photosensitive material is disclosed, wherein the electrophotographic photosensitive material comprises a photosensitive layer containing at least one thiophene compound selected from the group consisting of compounds having the general formulae (I) and (II):

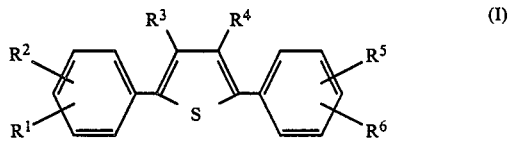

(I)

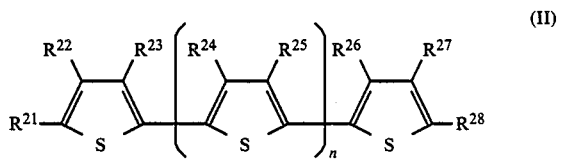

(II)

wherein $R^1$, $R^2$, $R^3$, $R^4$, $R^5$ and $R^6$, and $R^{21}$, $R^{22}$, $R^{23}$, $R^{24}$, $R^{25}$, and $R^{26}$ each represents a hydrogen or halogen atom or a hydroxy group, an alkyl group, a hydroxyalkyl group, an alkoxy group, an allyl group, a vinyl group, an acyl group, a formylakyl group, an acyloxy group, an alkoxycarbonyl group, an aryl group, a cyano group, a nitro group, an amino group, an alkylamino group or an arylamino group and n is an integer of 1, 2, 3, 4 or 5.

9 Claims, 1 Drawing Sheet

ELECTROPHOTOGRAPHIC PHOTOSENSITIVE MATERIAL CONTAINING THIOPHENE COMPOUND

FIELD OF THE INVENTION

This invention relates to an electrophotographic photosensitive material. More particularly, it relates to an electrophotographic photosensitive material which contains a specific thiophene compound in the photosensitive layer formed on an electroconductive substrate.

BACKGROUND OF THE INVENTION

Photosensitive materials so far used in electrophotographic photosensitive materials (hereinafter also referred to as photosensitive materials) include inorganic photoconductive substances, such as selenium and selenium alloys, dispersions of inorganic photoconductive substances, such as zinc oxide and cadmium sulfide, in resin binders, organic photoconductive substances, such as poly-N-vinylcarbazole and polyvinyl-anthracene, organic photoconductive substances, such as phthalocyanine compounds and bisazo compounds, and dispersions of such organic photoconductive substances in resin binders.

Photosensitive materials are required to have the function of holding surface charges in the dark, the function of receiving light and generating charges and the function of receiving light and transporting charges. There are two kinds of photosensitive materials, namely the so-called monolayer type photosensitive material consisting of one single layer having all the three functions and the so-called laminate type photosensitive material composed of functionally distinguishable layers, namely a layer which contributes mainly to charge generation and a layer which contributes mainly to retention of surface charges in the dark and charge transport upon receiving light. In electrophotographic image formation using these photosensitive materials, the technique of Carlson, for example, is applied. Image formation by this technique includes charging of the photosensitive material by corona discharge in the dark, formation of latent electrostatic images (e.g. letters, pictures) by illumination of the charged photosensitive material surface, development of the latent electrostatic images thus formed with a toner and fixation of the developed toner images on a supporting material, such as a paper sheet, following transfer thereto. After toner image transfer, the photosensitive material is subjected to the steps of charge removal, removal of remaining toner (cleaning), neutralization of residual charge by means of light (erasure), and so on, and then submitted to reuse.

In recent years, electrophotographic photosensitive materials in which organic materials are used have been put to practical use because of their advantageous features such as flexibility, thermal stability and film forming property. Thus, for example, there may be mentioned photosensitive materials comprising poly-N-vinylcarbazole and 2,4,7-trinitrofluorene-9-one (described in U.S. Pat. No. 3,484,237), photosensitive materials in which an organic pigment is used as the main component (described in Japanese Patent Application (OPI) No. 37543/1972) (the term "OPI" as used herein means "unexamined published Japanese Patent Application") and photosensitive materials in which a eutectic complex is used as the main component (Japanese Patent Application (OPI) No. 10735/1972). A number of novel hydrazone compounds have also been put to practical use.

However, although organic materials have a number of advantageous featues as compared with inorganic materials, none of organic materials can fully meet all requirements set forth with respect to the characteristic properties of photosensitive materials for electrophotography. Organic materials are still unsatisfactory particularly in respect of photosensitivity and of characteristics at the time of continuous repeated use.

SUMMARY OF THE INVENTION

Accordingly, it is an object of the invention, which has been made in view of the foregoing, to provide a photosensitive material for use in electrophotographic copies and printers, which has high sensitivity and shows good characteristics in repeated use, through the use, as a charge transporting substance in the photosensitive layer, of a novel organic material that has not yet been used.

In accordance with the present invention, the above object can be accomplished by providing a photosensitive material for use in electrophotography which has a photosensitive layer containing at least one thiophene compound selected from the group consisting of those thiophene compounds that are represented by the following general formulae (I) and (II),

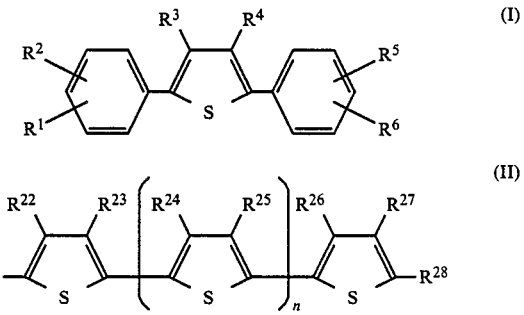

wherein $R^1$, $R^2$, $R^3$, $R^4$, $R^5$ and $R^6$, and $R^{21}$, $R^{22}$, $R^{23}$, $R^{24}$, $R^{25}$, $R^{26}$, $R^{27}$ and $R^{28}$ each represent a hydrogen or halogen atom or a hydroxy group, a hydroxyalkyl group, an alkyl group, an alkoxy group, an allyl group, a vinyl group, an acyl group, a formylalkyl group, an acyloxy group, an alkoxycarbonyl group, an aryl group, a cyano group, a nitro group, an amino group, an alkylamino group or an arylamino group and n is an integer of 1, 2, 3, 4 or 5.

DETAILED DESCRIPTION OF THE INVENTION

Figure 1:
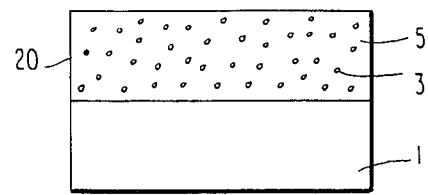
FIGS. 1–3 each is a schematic cross-sectional representation of a photosensitive material of the invention. The three embodiments shown differ in mode from one another. In the figures, an electroconductive substrate is indicated by reference number 1, a charge generating substance by 3, a charge generating layer by 4, a charge transporting substance by 5, a charge transporting layer by 6, a covering layer by 7, and a photosensitive layer by 20, 21 or 22.

In $R^1$ to $R^6$ and $R^{21}$ to $R^{28}$ of the formulae (I) and (II), the hydroxyalkyl group is preferably a hydroxyalkyl group having from 1 to 10 carbon atoms, and more preferably having from 1 to 5 carbon atoms, and for example a hydroxymethyl group, a hydroxyethyl group, etc.; the alkyl group is preferably an alkyl group having from 1 to 10 carbon atoms, and more preferably having from 1 to 5 carbon atoms, for example, a methyl group, an ethyl group, a propyl group, etc.; the halogen atom is preferably a chlorine atom, a bromine atom, etc.; the alkoxy group is preferably an alkoxy group having from 1 to 10 carbon atoms and more preferably having from 1 to 5 carbon atoms, for example, a methoxy group, an ethoxy group, a propoxy group, etc.; the acyl group is preferably an acyl group having from 1 to 10 carbon atoms, and more preferably from 1 to 5 carbon atoms, for example, a formyl group, an acetyl group, a propionyl group, etc.; the formylalkyl group is preferably a formylalkyl group having from 2 to 10 carbon atoms, and more preferably having from 2 to 5 carbon atoms, for example, a formylmethyl group, a formylethyl group, etc.; the acyloxy group is preferably an acyloxy group having from 1 to 10 carbon atoms, and more preferably from 1 to 5 carbon atoms, for example, a carboxy group, an acetoxy group, a propionyloxy group, etc.; the alkoxycarbonyl group is preferably an alkoxycarbonyl group having from 2 to 10 carbon atoms, and more preferably from 2 to 5 carbon atoms, for example, a methoxycarbonyl group, an ethoxycarbonyl group, etc.; the aryl group is preferably an aryl group having from 6 to 18 carbon atoms, for example, a phenyl group, a naphthyl group, etc.; the alkylamino group is preferably a dialkylamino group wherein the alkyl moiety has from 1 to 5 carbon atoms, for example, dimethylamino group, diethylamino group, etc.; the arylamino group is preferably a diarylamino group having from 6 to 12 carbon atoms, for example, diphenylamino group, etc.

Further, $R^1$ to $R^6$ and $R^{21}$ to $R^{28}$ in the formulae (I) and (II) each may be substituted by an alkoxy group having from 1 to 5 carbon atoms, an alkyl group having from 1 to 5 carbon atoms, an aryl group having from 6 to 18 carbon atoms, and a halogen atom such as a chlorine atom and a bromine atom.

Preferable thiophene compounds represented by the general formula (I) include thiophene compounds represented by the following general formula (III), (IV) and (V);

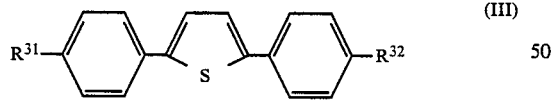

(III)

wherein, $R^{31}$ and $R^{32}$ each represents a hydrogen atom, a halogen atom, an alkyl group, an alkoxy group, a nitro group or, an amino group,

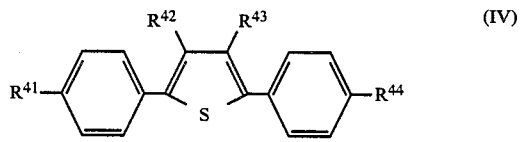

(IV)

wherein, $R^{41}$, $R^{42}$, $R^{43}$, and $R^{44}$ each represents a hydrogen atom, a halogen atom, an alkyl group, an alkoxy group, an aryl group, a nitro group, or an amino group.

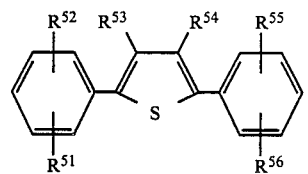

(V)

wherein $R^{51}$ to $R^{56}$ each represents a hydrogen or halogen atom or a hydroxy group, a hydroxyalkyl group, an alkyl group, an alkoxy group, an allyl group, a vinyl group, an acyl group, a formylalkyl group, an acyloxy group, an alkoxycarbonyl group, an aryl group, a cyano group, a nitro group, a amino group, an alkylamino group or an arylamino group.

In the above formulae (III), (IV) and (V), the halogen atom, the alkyl group, the alkoxy group, the aryl group, the hydroxyalkyl group, the acyl group, the formylalkyl group, the acyloxy group and the alkoxycarbonyl group each preferably includes the same as those defined in the formulae (I) and (II).

The thiophene compounds of general formulae (I) and (II) to be used in accordance with the invention are known materials and method for their synthesis have been described in the literature. As mentioned above, however, the use thereof in photosensitive layer has not been described as yet. In the course of their intensive study of various organic materials as made in an attempt to achieve the above object, the present inventors conducted a large number of experiments with such thiophene compounds and, as a result, found that the use of the above-mentioned thiophene compounds of general formulae (I) and (II) as charge transporting substances in photosensitive layers can give photosensitive materials having high sensitivity and excellent repeated-use characteristics.

Specific examples of the diphenylthiophenes of general formulae (I) and (II), which are to be used in accordance with the invention, are as follows:

| | Compound No. |
|---|---|
| ![structure] | No. I-1 |
| ![structure with Br] | No. I-2 |
| ![structure with Br, Br] | No. I-3 |
| ![structure with CH3, CH3] | No. I-4 |
| ![structure with CH3O, OCH3] | No. I-5 |

-continued

| Compound No. |
|---|
| No. I-6 |
| No. I-7 |
| No. I-8 |
| No. I-9 |
| No. I-10 |
| No. I-11 |
| No. I-12 |
| No. I-13 |
| No. I-14 |
| No. I-15 |

-continued

| Compound No. |
|---|
| No. I-16 |
| No. I-17 |
| No. I-18 |
| No. I-19 |
| No. I-20 |
| No. I-21 |
| No. I-22 |

| Compound No. |
|---|
| No. I-23 |
| No. I-24 |
| No. I-25 |
| No. I-26 |
| No. I-27 |
| No. I-28 |

Examples of the terthiophenes of (II), which are suited for use in the practice of the invention, are given below:

| Compound No. |
|---|
| No. II-1 |
| No. II-2 |
| No. II-3 |
| No. II-4 |
| No. II-5 |
| No. II-6 |
| No. II-7 |

-continued
| | Compound No. |
|---|---|
| 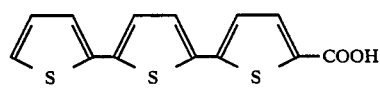 | No. II-8 |
| 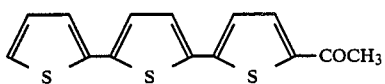 | No. II-9 |
| 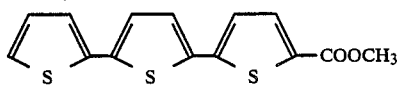 | No. II-10 |
| 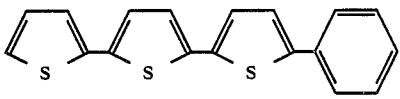 | No. II-11 |
| 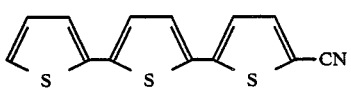 | No. II-12 |
| 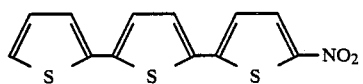 | No. II-13 |
| 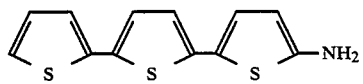 | No. II-14 |
| 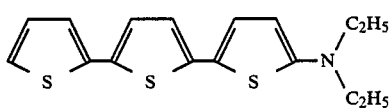 | No. II-15 |
| 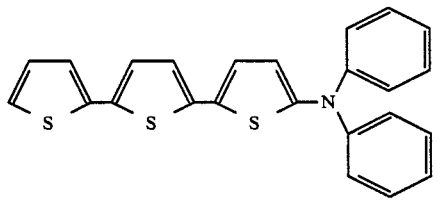 | No. II-16 |
| 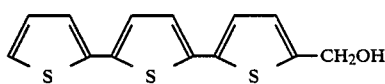 | No. II-17 |
| 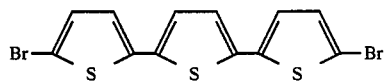 | No. II-18 |
| 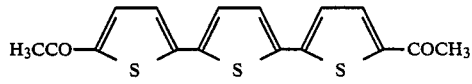 | No. II-19 |
| 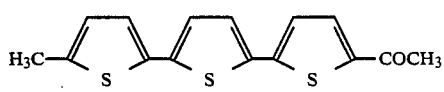 | No. II-20 |
| 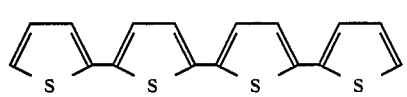 | No. II-21 |

-continued
| | Compound No. |
|---|---|
| 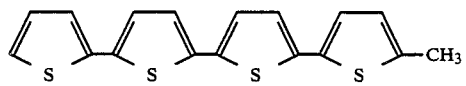 | No. II-22 |
| 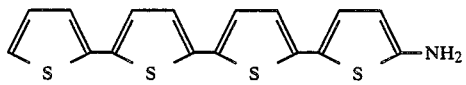 | No. II-23 |
|  | No. II-24 |
| 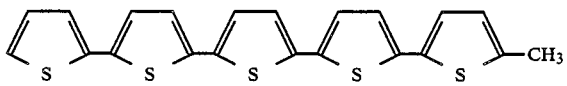 | No. II-25 |
| 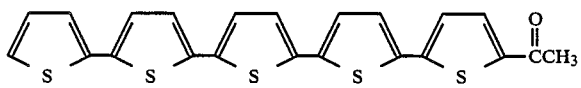 | No. II-26 |
| 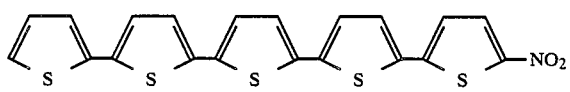 | No. II-27 |
| 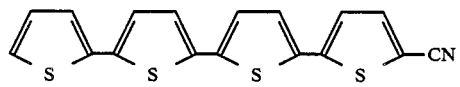 | No. II-28 |
|  | No. II-29 |
|  | No. II-30 |
| 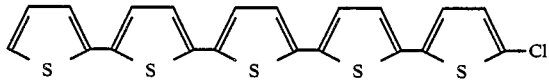 | No. II-31 |
| 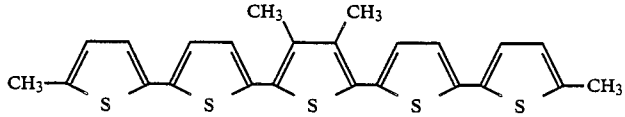 | No. II-32 |
| 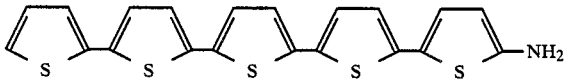 | No. II-33 |
| 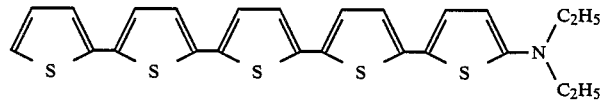 | No. II-34 |
|  | No. II-35 |
| 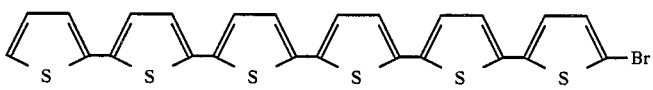 | No. II-36 |

-continued

Compound No.

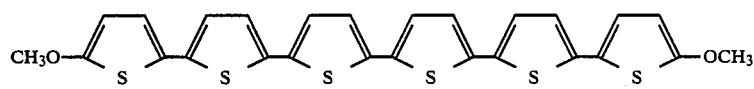

No. II-37

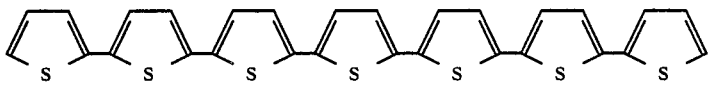

No. II-38

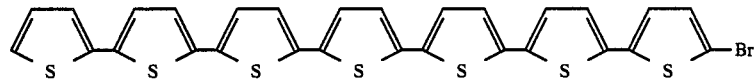

No. II-39

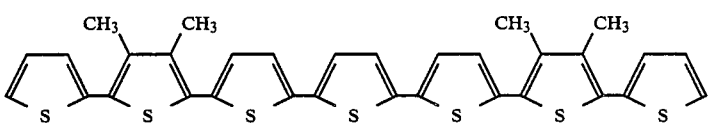

No. II-40

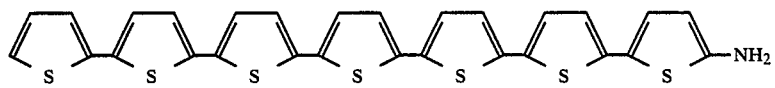

No. II-41

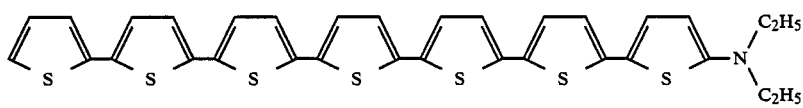

No. II-42

The thiophene compounds of general formulae (I) and (II) to be used in accordance with the invention can be synthesized by the procedure described, for example, in "Heterocyclies" Vol. 24, No. 5, 1986. The photosensitive material of the invention contains, as a charge transporting substance, a compound of general formulae (I) or (II) such as mentioned above in the photosensitive layer thereof. According to the mode of use of the thiophene compound, three embodiments of the photosensitive material a shown in FIGS. 1 to 3 are possible.

Figure 2:
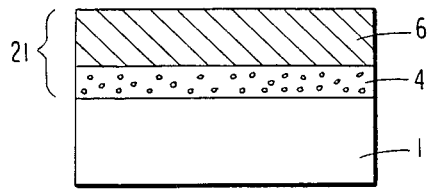
Figure 3:
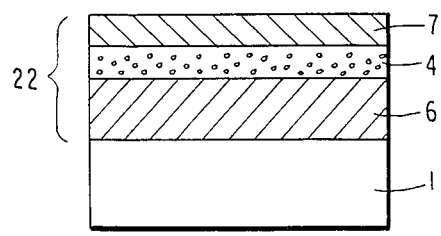

FIGS. 1 to 3 are schematic cross-sectional views of different embodiments of the photosensitive material of this invention. In the figures, the reference number 1 indicates an electroconductive substrate, 20, 21 and 22 each a photosensitive layer, 3 a charge generating substance, 4 a charge generating layer, 5 a charge transporting substance, 6 a charge transport layer, and 7 a covering layer.

In the embodiment shown in FIG. 1, a photosensitive layer 20 consisting of a dispersion of a charge generating substance 3 and a charge transporting substance 5, i.e. the thiophene compound, in a binder resin is disposed on an electroconductive substrate 1. Such a construction is generally referred to as a monolayer type photosensitive material.

In the embodiment shown in FIG. 2, a photosensitive layer 21 which is a laminate of a charge generating layer 4 mainly composed of a charge generating substance 3 and a charge transport layer 6 containing a charge transporting substance 5 (i.e. the thiophene compound) is disposed on an electroconductive substrate 1. Such a construction is generally referred to as an integlated layer type photosensitive material.

In the embodiment shown in FIG. 3, the layer construction is reversed as compared with that shown in FIG. 2. In the case of this construction, a covering layer 7 is generally disposed for the protection of the charge generating layer 4. The photosensitive layer 22 is composed of the charge transport layer 6, charge generating layer 4 and the covering layer 7.

The two kinds of layer construction as shown in FIG. 2 and FIG. 3 are used because the photosensitive material is used in the positive or negative charge mode. Generally, however, the layer construction shown in FIG. 2 is used in the negative charge mode. Even if it is desired to use the layer construction shown in FIG. 2 in the positive charge mode, no appropriate charge transporting substance is available at present. Therefore, for use in the positive charge mode, the layer construction shown in FIG. 3 should be employed as an effective one, as already proposed by the present inventors.

The photosensitive material shown in FIG. 1 can be prepared by dispersing a charge generating substance in a solution containing a charge transporting substance and a binder resin and applying the dispersion to an electroconductive substrate.

The photosensitive material shown in FIG. 2 can be prepared by vacuum-depositing a charge generating substance on an electronconductive substrate or by applying a dispersion of a charge generating substance in particle form in a solvent or a binder resin to an electroconductive substrate, drying the coat layer and further applying a solution containing a charge transporting substance and a binder resin onto said coat layer, followed by drying.

The photosensitive material shown in FIG. 3 can be prepared by applying a solution containing a charge transporting substance and a binder resin to an electroconductive substrate and drying, then vacuum-depositing a charge generating substance thereon or by applying a dispersion of a charge generating substance in particle form in a solvent or a binder resin and drying, and further providing a covering layer 7.

The electroconductive substrate 1 serves as an electrode of the photosensitive material and at the same time as the substrate for each layer. It may be in the form of cylinder, sheet or film and may be made of a metal such as aluminum, stainless steel or nickel or of glass, a resin or the like as electroconductively surface-treated.

As mentioned above, the charge generating layer 4 is formed by applying a dispersion of a charge generating substance 3 in particle form, in a binder resin or by the technique of vacuum vapor phase deposition or the like. Said layer 4 accepts light and generates charges. It is important that said layer have high charge generating efficiency and, at the same time, that the charges generated be injected into the charge transport layer 6 and covering layer 7. It is desirable that the injection be as little dependents as possible on the electric field and be sufficient even in low intensity electric fields. Useful as the charge generating substance are metal-free phthalocyanine, titanylphthalocyanine, other phthalocyanine compounds, various azo, quinone, and indigo pigments, selenium, and selenium compounds, among others. Appropriate substances can be selected depending on the light wavelength region of the exposure light source used for image formation. The charge generating layer is only required to be capable of generating charges and, therefore, the layer thickness depends on the light absorption coefficient of the charge generating substance and generally is not more than 5 $\mu m$, preferably not more than 1 $\mu m$.

An amount of the charge generating substance used in the present invention is determined according to a desired characteristic of the electrophotographic material, and is preferably 10 wt% or more, more preferably 20 to 100 wt%, in a charge generating layer.

It is also possible to form the charge generating layer using the charge generating substance in admixture with a minor proportion of a charge transporting substance such as thiophenes used in the present invention, oxazoles, oxadiazoles and stilbene compound, etc. and so forth. A proportion of the charge transporting substance to the charge generating substance is preferably from 0.1 to 0.8 by weight. Usable resin as the binder are polycarbonates, polyesters, polyamides, polyurethanes, epoxy resins, silicone resins, methacrylic ester homopolymers and copolymers produced by copolymerizing a monomer derived from the above polymers with a comonomer such as stylene, methacrylate, etc., for instance, either alone or in appropriate combinations.

In the monolayer type photosensitive material, the photosensitive layer contains at least one charge generating substance in an amount of from 10 to 60 wt% based on a binder and at least one hydrazone compound in an amount of from 10 to 60 wt% based on a binder.

The charge transport layer 6 is a layer produced by coating on an electroconductive substrate a dispersion of the thiophene compound of general formulae (I) or (II) in a binder resin, which is to serve as a charge transporting substance. A preferable thickness of the charge transporting layer is preferably from 5 to 30 $\mu m$, and more preferably 10 to 20 $\mu m$. An amount of the charge transporting substance used in the present invention is selected according to a desired characteristic of the electrophotographic photosensitive material, and is preferably from 20 to 80 wt% in a charge transporting layer. In the dark, said layer serves as an insulator layer and retains electrostatic charges on the photosensitive material and, upon acceptance of light, transport the charges injected from the charge generating layer. Usable as the binder resin are polycarbonates, polyesters, polyamides, polyurethanes, epoxy resins, silicone resins, methacrylic ester homopolymers and copolymers, among others.

The covering layer 7, in the dark, accepts charges generated by corona discharge and retains them. It is necessary that said layer be capable of transmitting light to which the charge generating layer should respond and that said layer be capable of transmitting light at the time of exposure to thereby allow the light to reach the charge generating layer so that the surface charges can be neutralized and disappear upon injection of charges generated in the charge generating layer. Usable as the covering material are film-forming insulator materials such as polyesters and polyamides. Furthermore, such organic materials can be used in admixture with inorganic materials such as glass resins and $SiO_2$ or, further, materials which reduce the electric resistance, such as metals and metal oxides. The covering material is not limited to organic film-forming insulator materials but it is also possible to form the covering layer by using an inorganic material such as $SiO_2$ or by applying a metal, metal oxide such as Zn, Sn, Ti, ZnO, $SnO_2$, $TiO_2$, etc. or the like by the technique of vapor phase deposition or sputtering, for instance. The covering material should desirably be as transparent as possible in the wavelength region corresponding to the absorption maximum of the charge generating substance.

The thickness of the covering layer may vary depending on the composition thereof but generally is optional uses the covering layer produces an adverse effect, for example causes an increase in residual potential in repreated continuous use.

The following examples are further illustrative of the present invention.

EXAMPLE I-1

A coating liquid was prepared by kneading in a mixer 50 weight parts of 50 weight parts of metal-free phthalocyanine (available from Tokyo Kasei Kogyo) pulverized beforehand in a ball mill for 150 hours, 100 weight parts of the diphenylthiophene compound No. I-1, a polyester resin (Vylon; available from Toyobo Co., Ltd.) and the solvent tetrahydrofuran (THF) for 3 hours. A photosensitive layer ws formed, in a dry thickness of 15 $\mu m$, on an aluminum-deposited polyester film (Al-PET) (electroconductive substrate) by applying the coating liquid to the substrate by the wire bar technique. Thus was prepared a photosensitive material.

EXAMPLE I-2

First, $\alpha$-form metal-free phthalocyanine (starting material) was micropulverized in a LIMMAC (linear induction motor mixing and crushing) apparatus (Fuji Electric Co., Ltd.), where the $\alpha$-form metal-free phthalocyanine was crushed in a nonmagnetic can containing Teflon pieces as working bodies, with said can disposed between two opposing linear motors, for 20 minutes. One weight parts of the thus-micropulverized samples was dispersed in 50 weight parts of the solvent DMF (N,N-dimethylformamide) by ultrasonic treatment. The metal-free phthalocyanine sample was separated from the solvent by filtration and dried.

Then, a coating solution was prepared by mixing a solution of 100 weight parts of the diphenylthiophene compound No. I-1 in 700 weight parts of tetrahydrofuran (THF) and a solution of 100 weight parts of polymethyl methacrylate polymer (PMMA; available from Tokyo Kasei Kogyo) in 700 weight parts of toluene. A charge transport layer was formed, in a dry thickness of 15 μm, on an aluminum-deposited polyester film substrate by applying the coating solution to said substrate using a wire bar. On the thus-obtained charge transport layer, there was formed a charge generating layer in a dry thickness of 1 μm by applying, with a wire bar, a coating liquid prepared by kneading in a mixer 50 weight part of the metal-free phthalocyanine treated in the above manner, 50 weight parts of a polyester resin (Vylon-200 ®; available from Toyobo Co., Ltd.), and the solvent THF for 3 hours. Thus was prepared a photosensitive material.

EXAMPLE I-3

A photosensitive material was prepared by forming a photosensitive layer in the same manner as in Example I-1 except that the composition of the charge generating layer was as follows: 50 weight parts of metal-free phthalocyanine, 100 weight parts of the thiophene compound No. I-1, and 50 weight parts of a polyester resin (Vylon 200; Toyobo Co., Ltd.).

EXAMPLE I-4

A photosensitive material was prepared by forming a photosensitive layer in the same manner as in Example I-3 except that Chlorodiane Blue, a bisazo pigment, as described in Japanese Patent Application (OPI) No. 37543/1972, was used in lieu of metal-free phthalocyanine.

The thus-obtained photosensitive materials were measured for their electrophotographic characteristics using an electrostatic recording paper testing apparatus (Kawaguchi Denki model SP-428).

The surface potential Vs (volts) of each photosensitive material is the initial surface potential attained upon positively charging the photosensitive material surface by +6.0 kV corona discharging in the dark for 10 seconds. After allowing the material to stand in the dark for 2 seconds following discontinuation of the corona discharge, the surface potential $V_d$ (volts) was measured. The photosensitive material surface was then further irradiated with white light at an illuminance of 2 lux, and the time (ins econds) required for the illumination to discharge the material surface to half of $V_d$ was measured and the half decay exposure amount $E_{\frac{1}{2}}$ (lux·sec) was calculated. The residual potential $V_r$ (volts) is the surface potential after 10 seconds of irradiation with white light at an illuminance of 2 lux. Since the use of the phthalocyanine compound as the charge generating substance was expected to give high sensitivity to long wavelength light, the electrophotographic characteristics obtainable by the use of monochromatic light of the wavelength 780 nm were also measured. Thus, the same procedure as above was followed until Vd measurement, then 1 μW monochromatic light (780 nm) was used in lieu of white light for irradiation, and the half decay exposure amount (μJ/cm$^2$) was determined. Further, after irradiation of the photosensitive material surface with said light for 10 seconds, the residual potential Vr (volts) was measured. The results of the measurements are shown in Table I-1.

TABLE I-1

| Example | White light | | | Light of wavelength 780 nm | | |
|---|---|---|---|---|---|---|
| | $V_s$ Volts | $V_r$ Volts | $E_{\frac{1}{2}}$ Lux·sec | $V_s$ Volts | $V_r$ Volts | $E_{\frac{1}{2}}$ μJ/cm$^2$ |
| I-1 | 500 | 60 | 3.8 | 580 | 50 | 2.2 |
| I-2 | 800 | 90 | 4.5 | 780 | 70 | 2.0 |
| I-3 | 780 | 70 | 3.5 | 740 | 60 | 1.5 |
| I-4 | 810 | 90 | 3.8 | — | — | — |

As can be seen in Table I-1, the photosensitive materials of Examples I-1, I-2, I-3 and I-4 were comparable to one another with respect to half decay exposure and residual potential and were good also with respect to surface potential.

EXAMPLE I-5

A charge generating layer was formed on an aluminum plate having a thickness of 500 μm by vacuum deposition of selenium to a thickness of 1.5 μm. Thereon was then formed a charge transport layer by applying, with a wire bar, a coating solution prepared by mixing a solution of 100 weight parts of the diphenylthiophene compound No. I-2 in 700 weight parts of tetrahydrofuran (THF) and a solution of 100 weight parts of polymethyl methacrylate (PMMA; Tokyo Kasei Kogyo) in 700 weight parts of toluene of give a dry layer thickness of 20 μm. When subjected to −6.0 kV corona discharge for 0.2 second, the photosensitive material obtained gave good results as follows: $V_s = -880$ V, $V_r = 140$ V, and $E_{\frac{1}{2}} = 5.2$ lux·sec.

EXAMPLE I-6

A coating liquid was prepared by kneading in a mixer 50 weight parts of metal-free phthalocyanine treated in the same manner as in Example I-1, 50 weight parts of a polyester resin (Vylon 200, Toyobo Co., Ltd.), and the solvent THF. A charge generating layer was formed, in a dry thickness of about 1 μm, on an aluminum support by applying the coating liquid to said support. Then, a charge transport layer, about 15 μm in thickness, was formed by applying a mixture of 100 weight parts of the diphenylthiophene compound No. I-3, 100 weight parts of a polycarbonate resin (Panlite L-1250), 0.1 weight part of a silicone oil and 700 weight parts of THF onto the charge generating layer.

When subjected to −6.0 kV corona discharge for 0.2 second in the same manner as in Example I-4, the photosensitive material obtained gave good results as follows: $V_s = -820$ V, $E_{\frac{1}{2}} = 3.8$ lux·sec.

EXAMPLE I-7

A photosensitive material was prepared in the same manner as in Example I-2 except that an aluminum drum, 60 mm in outside diameter and 320 mm in length, was used as the electroconductive substrate in place of the aluminum-deposited polyester film (Al-PET) and that the charge transport layer (15 μm) and charge generating layer (2 μm) were formed on the exterior surface of the drum by dip coating.

The photosensitive material prepared in Example I-7 was mounted on a Carlson-system copier and evaluated by producing 100 copies successively. Good copies were obtained without image density decrease or background stain. The photosensitive material prepared in Example I-7 was mounted on the same copier, the developing section was removed, surface potentiometes were provided, and potential changes during the copying process were measured. The results thus obtained are shown in Table I-2.

TABLE I-2

| | Potential in the dark (volts) | | Potential in the illuminated portion (volts) | |
|---|---|---|---|---|
| Example | 1st copying operation | 100th copying operation | 1st copying operation | 100th copying operation |
| I-7 | 790 | 740 | 120 | 140 |

For both the potentials, the repeated-use characteristics were satisfactory.

EXAMPLE II-1

A coating liquid was prepared by kneading in a mixer 50 weight parts of 50 weight parts of metal-free phthalocyanine (available from Tokyo Kasei Kogyo) pulverized beforehand in a ball mill for 150 hours, 100 weight parts of the diphenylthiophene compound No. I-8 specified above, a polyester resin (Vylon; available from Toyobo Co., Ltd.) and the solvent tetrahydrofuran (THF) for 3 hours. A photosensitive layer was formed, in a dry thickness of 15 μm, on an aluminum-deposited polyester film (Al-PET) (electronconductive substrate) by applying the coating liquid to the substrate by the wire bar technique. Thus was prepared a photosensitive material.

EXAMPLE II-2

First, α-form metal-free phthalocyanine (starting material) was micropulverized in a LIMMAC (linear) induction motor mixing and crushing) apparatus (Fuji Electric Co., Ltd.), where the α-form metal-free phthalocyanine was crushed in a nonmagnetic can containing Teflon pieces as working bodies, with said can disposed between two opposing linear motors, for 20 minutes. One weight part of the thus-micropulverized samples was dispersed in 50 weight parts of the solvent DMF (N,N-dimethylformamide) by ultrasonic treatment. The metal-free phthalocyanine sample was separated from the solvent by filtration and dried.

Then, a coating solution was prepared by mixing a solution of 100 weight parts of the diphenylthiophene No. I-8 mentioned above in 700 weight parts of tetrahydrofuran (THF) and a solution of 100 weight parts of polymethyl methacrylate polymer (PMMA; available from Tokyo Kasei Kogyo) in 700 weight parts of toluene. A charge transport layer was formed, in a dry thickness of 15 μm, on an aluminum-deposited polyester film substrate by applying the coating solution to said substrate using a wire bar. On the thus-obtained charge transport layer, there was formed a charge generating layer in a dry thickness of 1 μm by applying, with a wire bar, a coating liquid prepared by kneading in a mixer 50 weight parts of the metal-free phthalocyanine treated in the above manner, 50 weight parts of a polyester resin (Vylon 200; available from Toyobo Co., Ltd.); and the solvent THF for 3 hours. After drying, there was obtained a photosensitive material.

EXAMPLE II-3

A photosensitive material was prepared by forming a photosensitive layer in the same manner as in Example II-1 except that the composition of the charge generating layer was as follows: 50 weight parts of metal-free phthalocyanine, 100 weight parts of the diphenylthiophene compound No. I-8, 50 weight parts of a polyester resin (Vylon 200; Toyobo Co., Ltd.) and 50 weight parts of PMMA.

EXAMPLE II-4

A photosensitive material was prepared by forming a photosensitive layer in the same manner as in Example II-3 except that Chlorodiane Blue, a bisazo pigment, was used in lieu of metal-free phthalocyanine.

The thus-obtained photosensitive materials were measured for their electrophotographic characteristics using an electrostatic recording paper testing apparatus (Kawaguchi Denki model SP-428) according to the procedure of Example I-4. The results of the measurements are shown in Table II-1.

TABLE II-1

| | White light | | | Light of wavelength 780 nm | | |
|---|---|---|---|---|---|---|
| Example | $V_s$ Volts | $V_r$ Volts | $E_\frac{1}{2}$ Lux·sec | $V_s$ Volts | $V_r$ Volts | $E_\frac{1}{2}$ μJ/cm² |
| II-1 | 600 | 60 | 2.8 | 650 | 40 | 1.5 |
| II-2 | 780 | 80 | 2.5 | 740 | 60 | 1.8 |
| II-3 | 750 | 50 | 2.1 | 720 | 30 | 1.3 |
| II-4 | 820 | 80 | 2.8 | — | — | — |

As can be seen in Table II-1, the photosensitive materials of Examples II-1, II-2, II-3 and II-4 were comparable to one another with respect to half decay exposure amount and residual potential and were good also with respect to surface potential.

EXAMPLE II-5

A charge generating layer was formed on an aluminum plate having a thickness of 500 μm by vacuum vapor deposition of selenium to a thickness of 1.5 μm. Thereon was then formed a charge transport layer by applying, with a wire bar, a coating solution prepared by mixing a solution of 100 weight parts of the diphenylthiophene compound No. I-9 in 700 weight parts of tetrahydrofuran (THF) and a solution of 100 weight parts of polymethyl methacrylate (PMMA; Tokyo Kasei Kogyo) in 700 weight parts of toluene to give a dry layer thickness of 20 μm. When subjected to −6.0 kV corona discharge for 0.2 second, the photosensitive material obtained gave good results as follows: $V_s = -840$ V, $V_r = 80$ V, and $E_\frac{1}{2} = 3.2$ lux·sec.

EXAMPLE II-6

A coating liquid was prepared by kneading in a mixer 50 weight parts of metal-free phthalocyanine treated in the same manner as in Example II-1, 50 weight parts of a polyester resin (Vylon 200, Toyobo Co., Ltd.), and the solvent THF. A charge generating layer was formed, in a dry thickness of about 1 μm, on an aluminum support by applying the coating liquid to said support. Then, a charge transport layer, about 15 μm in thickness, was formed by applying a mixture of 100 weight parts of the diphenylthiophene compound No. I-10, 100 weight parts of a polycarbonate resin (Panlite L-1250), 0.1 weight part of a silicone oil, 700 weight parts of THF and 700 weight parts of toluene onto the charge generating layer.

When subjected to −6.0 kV corona discharge for 0.2 second in the same manner as in Example II-4, the photosensitive material obtained gave good results as follows: $V_s = -850$ V, $E_\frac{1}{2} = 2.5$ lux·sec.

EXAMPLE II-7

A photosensitive material was prepared in the same manner as in Example II-2 except that an aluminum drum, 60 mm in outside diameter and 320 mm in length, was used as the electroconductive substrate in place of th aluminum-deposited polyester film (Al-PET) and that the charge transport layer (15 μm) and charge generating layer (2 μm) were formed on the exterior surface of the drum by dip coating.

The photosensitive material prepared in Example II-7 was mounted on a Carlson-system copier and evaluated by producing 100 copies successively. Good copies were obtained without image density decrease or paper sheet staining. The photosensitive material prepared in Example II-7 was mounted on the same copier, the developing section was removed, surface potentiometers were provided, and potential changes during the copying process were measured. The results thus obtained are shown in Table II-2.

TABLE II-2

| Example | Potential in the dark (volts) | | Potential in the illuminated portion (volts) | |
|---|---|---|---|---|
| | 1st copying operation | 100th copying operation | 1st copying operation | 100th copying operation |
| II-7 | 850 | 830 | 80 | 90 |

As can be seen in Table II-2, the above photosensitive materials showed good repeated-use characteristics.

EXAMPLE III-1

First, α-form metal-free phthalocyanine (starting material) was micropulverized in a LIMMAC (linear induction motor mixing and crushing) apparatus (Fuji Electric Co., Ltd.), where the α-form metal-free phthalocyanine was crushed in a nonmagnetic can containing Teflon pieces as working bodies, with said can disposed between two opposing linear motors, for 20 minutes. One weight parts of the thus-micropulverized samples was dispersed in 50 weight parts of the solvent DMF (N,N-dimethylformamide) by ultrasonic treatment. Thereafter, the sample was separated from DMF by filtration and then dried. To the dried sample, there was added 3 weight parts of X-form metal-free phthalocyanine, followed by further addition of 10 weight parts of a pyrazoline compound (ASPP®, available from Taoka Chemical), a polyester resin (Vylon 200®, available from Toyobo Co., Ltd.) and 790 weight parts of tetrahydrofuran (THF). The mixture was shaken vigorously with SUS balls and further subjected to ultrasonic treatment for 30 minutes to give a coating liquid for charge generating layer formation. Separately, a coating solution for charge transport layer formation was prepared by mixing a solution of 1 weight part of the terthiophene No. II-1 shown hereinabove in 6 weight parts of tetrahydrofuran (THF) with a solution of 1.5 weight parts of polymethyl methacrylate polymer (PMMA; available from Tokyo Kasei Kogyo) in 13.5 weight parts of toluene. An aluminum-deposited polyester film was coated with both the coating compositions thus obtained to give a photosensitive member having a charge transport layer (15 μm) and a charge generating layer (2 μm).

EXAMPLE III-2

A photosensitive material was prepared in the same manner as in Example III-1 except that bromoterthiophene (Compound No. II-2) was used in lieu of terthiophene (Compound No. II-1).

EXAMPLE III-3

A photosensitive member was prepared in the same manner as in Example III-1 except that methylterthiophene (Compound No. II-4) was used in lieu of terthiophene (Compound II-1).

EXAMPLE III-4

A photosensitive material was prepared in the same manner as in Example III-1 except that terthiophenecarboxaldehyde (Compound No. II-7) was used in lieu of terthiophene (Compound No. II-1).

EXAMPLE III-5

A photosensitive material was prepared in the same manner as in Example III-1 except that acetylterthiophene (Compound No. II-9) was used in lieu of terthiophene (Compound No. II-1).

EXAMPLE III-6

A photosensitive material was prepared in the same manner as in Example III-1 except that terthiophenemethanol (Compound No. II-17) was used in lieu of terthiophene (Compound No. II-1).

EXAMPLE III-7

Chlorodiane Blue was micropulverized in a ball mill, where a glass pot and glass balls were used, for 100 hours. To 1 weight parts of the thus-micropulverized sample, there were added 2 weight parts of a pyrazoline compound (ASPP®, available from Taoka Chemical), 2 weight parts of a polyester resin (Vylon 200, Toyobo Co., Ltd.) and 96 weight parts of tetrahydrofuran (THF). After addition of SUS balls, the mixture was shaken vigorously for 2 hours and then further subjected to ultrasonic treatment for 30 minutes to give a coating liquid for charge generating layer formation. Separately, a coating solution for charge transport layer formation was prepared by mixing a solution of 1.5 weight parts of polymethyl methacrylate (PMMA, Tokyo Kasei Kogyo) in 13.5 weight parts of toluene. An aluminum-deposited polyester film was coated with both the coating compositions prepared in the above manner to give a photosensitive member having a charge transport layer (15 μm) and a charge generating layer (2 μm).

EXAMPLE III-8

A photosensitive member was prepared in the same manner as in Example III-7 except that bromoterthiophene (Compound No. II-2) was used in lieu of terthiophene (Compound No. II-1).

EXAMPLE III-9

A photosensitive member was prepared in the same manner as in Example III-7 except that methylterthiophene (Compound No. II-4) was used in lieu of terthiophene (Compound No. II-1).

EXAMPLE III-10

A photosensitive member was prepared in the same manner as in Example III-7 except that terthiophenecarboxaldehyde (Compound No. II-7) was used in lieu of terthiophene (Compound No. II-1).

EXAMPLE III-11

A photosensitive member was prepared in the same manner as in Example III-7 except that acetylterthiophene (Compound No. II-9) was used in lieu of terthiophene (Compound No. II-1).

EXAMPLE III-12

A photosensitive member was prepared in the same manner as in Example III-7 except that terthiophenemethanol (Compound No. II-17) was used in lieu of terthiophene (Compound No. II-1).

The thus-obtained photosensitive members were measured for their electrophotographic characteristics using an electrostatic recording paper testing apparatus (Kawaguchi Denki model SP-428) according to the procedure disclosed in Example I-4. In addition, since the use of Chlorodiane Blue as the charge generating substance was expected to result in high sensitivity to green color, electrophotographic characteristics measurement was made also using monochromatic light of the wavelength 550 nm in the same manner as in the case of phthalocyanine. The measurement results are shown in Table III-2.

TABLE III-1

| | White light | | | Light of wavelength 780 nm | | |
|---|---|---|---|---|---|---|
| Example | $V_s$ Volts | $V_r$ Volts | $E_{\frac{1}{2}}$ Lux · sec | $V_s$ Volts | $V_r$ Volts | $E_{\frac{1}{2}}$ μJ/cm² |
| III-1 | 550 | 80 | 4.5 | 570 | 50 | 3.4 |
| III-2 | 580 | 100 | 5.8 | 600 | 70 | 4.4 |
| III-3 | 590 | 120 | 5.6 | 610 | 100 | 4.8 |
| III-4 | 570 | 110 | 5.2 | 580 | 90 | 4.7 |
| III-5 | 560 | 100 | 4.9 | 570 | 80 | 3.8 |
| III-6 | 560 | 90 | 4.7 | 590 | 60 | 3.5 |

As can be seen in Table III-1, the photosensitive members of the above examples were comparable in half decay exposure amount and residual potential to one another and were good in surface potential as well.

TABLE III-2

| | White light | | | Light of wavelength 780 nm | | |
|---|---|---|---|---|---|---|
| Example | $V_s$ Volts | $V_r$ Volts | $E_{\frac{1}{2}}$ Lux · sec | $V_s$ Volts | $V_r$ Volts | $E_{\frac{1}{2}}$ μJ/cm² |
| III-7 | 530 | 100 | 5.1 | 600 | 60 | 4.1 |
| III-8 | 560 | 130 | 6.2 | 620 | 80 | 5.2 |
| III-9 | 550 | 110 | 6.0 | 640 | 100 | 5.8 |
| III-10 | 520 | 90 | 5.4 | 590 | 70 | 4.9 |
| III-11 | 540 | 120 | 5.7 | 610 | 90 | 5.3 |
| III-12 | 550 | 100 | 5.3 | 620 | 80 | 5.0 |

As can be seen in Table III-2, the photosensitive members of the above examples were comparable in half decay exposure amount and in residual potential to one another and were satisfactory in surface potential as well.

EXAMPLE IV-1

A coating liquid was prepared by kneading in a mixer 50 weight parts of 50 weight parts of metal-free phthalocyanine (available from Tokyo Kasei Kogyo) pulverized beforehand in a ball mill for 150 hours, 100 weight parts of the thiophene compound No. II-21 specified above, a polyester resin (Vylon; available from Toyobo Co., Ltd.) and the solvent tetrahydrofuran (THF) for 3 hours. A photosensitive layer was formed, in a dry thickness of 15 μm, on an aluminum-deposited polyester film (Al-PET) (electroconductive substrate) by applying the coating liquid to the substrate by the wire bar technique. Thus was prepared a photosensitive material.

EXAMPLE IV-2

First, α-form metal-free phthalocyanine (starting material) was micropulverized in a LIMMAC (linear induction motor mixing and crushing) apparatus (Fuji Electric Co., Ltd.), where the α-form metal-free phthalocyanine was crushed in a nonmagnetic can containing Teflon pieces as working bodies, with said can disposed between two opposing linear motors, for 20 minutes. One weight part of the thus-micropulverized samples was dispersed in 50 weight parts of the solvent DMF (N,N-dimethylformamide) by ultrasonic treatment. The metal-free phthalocyanine sample was separated from the solvent by filtration and dried.

Then, a coating solution was prepared by mixing a solution of 100 weight parts of the thiophene compound No. II-21 mentioned above in 700 weight parts of tetrahydrofuran (THF) and a solution of 100 weight parts of polymethyl methacrylate polymer (PMMA; available from Tokyo Kasei Kogyo) in 700 weight parts of toluene. A charge transport layer was formed, in a dry thickness of 15 μm, on an aluminum-deposited polyester film substrate by applying the coating solution to said substrate using a wire bar. On the thus-obtained charge transport layer, there was formed a charge generating layer in a dry thickness of 1 μm by applying, with a wire bar, a coating liquid prepared by kneading in a mixer 50 weight parts of the metal-free phthalocyanine treated in the above manner, 50 weight parts of a polyester resin (Vylon 200; available from Toyobo Co., Ltd.), and the solvent THF for 3 hours. After drying, there was obtained a photosensitive material.

EXAMPLE IV-3

A photosensitive material was prepared by forming a photosensitive layer in the same manner as in Example IV-1 except that the composition of the charge generating layer was as follows: 50 weight parts of metal-free phthalocyanine, 100 weight parts of the thiophene compound No. II-21, 50 weight parts of a polyester resin (Vylon 200; Toyobo Co., Ltd.) and 50 weight parts of PMMA.

EXAMPLE IV-4

A photosensitive material was prepared by forming a photosensitive layer in the same manner as in Example IV-3 except that Chlorodiane Blue as is shown in Japanese Patent Application (OPI) No. 37543/72, a bisazo pigment, was used in lieu of metal-free phthalocyanine.

The thus-obtained photosensitive materials were measured for their electrophotographic characteristics using an electrostatic recording paper testing apparatus (Kawaguchi Denki model SP-428) according to the procedure of Example I-4. The results of the measrurements are shown in Table IV-1.

TABLE IV-1

| | White light | | | Light of wavelength 780 nm | | |
|---|---|---|---|---|---|---|
| Example | $V_s$ Volts | $V_r$ Volts | $E_{\frac{1}{2}}$ Lux · sec | $V_s$ Volts | $V_r$ Volts | $E_{\frac{1}{2}}$ μJ/cm² |
| II-1 | 700 | 100 | 4.8 | 800 | 100 | 3.5 |
| II-2 | 730 | 70 | 4.1 | 750 | 70 | 4.7 |
| II-3 | 680 | 70 | 5.0 | 650 | 100 | 5.2 |

TABLE IV-1-continued

| | White light | | | Light of wavelength 780 nm | | |
|---|---|---|---|---|---|---|
| Example | $V_s$ Volts | $V_r$ Volts | $E_{\frac{1}{2}}$ Lux·sec | $V_s$ Volts | $V_r$ Volts | $E_{\frac{1}{2}}$ μJ/cm$^2$ |
| II-4 | 820 | 80 | 3.8 | — | — | — |

As can be seen in Table IV-1, the photosensitive materials of Examples IV-1, IV-2, IV-3 and IV-4 were comparable to one another with respect to half decay exposure amount and residual potential and were good also with respect to surface potential.

EXAMPLE IV-5

A charge generating layer was formed on an aluminum plate having a thickness of 500 μm by vacuum vapor deposition of selenium to a thickness of 1.5 μm. Thereon was then formed a charge transport layer by applying, with a wire bar, a coating solution prepared by mixing a solution of 100 weight parts of the thiophene compound No. II-22 in 700 weight parts of tetrahydrofuran (THF) and a solution of 100 weight parts of polymethyl methacrylate (PMMA; Tokyo Kasei Kogyo) in 700 weight parts of toluene to give a dry layer thickness of 20 μm. When subjected to −6.0 kV corona discharge for 0.2 second, the photosensitive material obtained gave good results as follows: $V_s = -740$ V, $V_r = -100$ V, and $E_{\frac{1}{2}} = 5.1$ lux·sec.

EXAMPLE IV-6

A coating liquid was prepared by kneading in a mixer 50 weight parts of metal-free phthalocyanine treated in the same manner as in Example IV-1, 50 weight parts of a polyester resin (Vylon 200, Toyobo Co., Ltd.), and the solvent THF. A charge generating layer was formed, in a dry thickness of about 1 μm, on an aluminum support by applying the coating liquid to said support. Then, a charge transport layer, about 15 μm in thickness, was formed by applying a mixture of 100 weight parts of the thiophene compound No. II-23, 100 weight parts of a polycarbonate resin (Panlite L-1250), 0.1 weight part of a silicone oil, 700 weight parts of THF and 700 weight parts of toluene onto the charge generating layer.

When subjected to −6.0 kV corona discharge for 0.2 second in the same manner as in Example IV-5, the photosensitive material obtained gave good results as follows: $V_s = -680$ V, $E_{\frac{1}{2}} = 5.5$ lux·sec.

EXAMPLE IV-7

Photosensitive materials were prepared in the same manner as in Example IV-7 except that the thiophene compounds Nos. II-24 to II-42 specifically shown hereinabove were used in lieu of the thiophene compound No. II-21.

The photosensitive materials were subjected to +6.0 kV corona discharge in the dark for 10 seconds and then illuminated with white light at an illuminance of 2 lux. The half decay exposure data ($E_{\frac{1}{2}}$) thus obtained are shown in Table IV-2.

TABLE IV-2

| Compound No. | $E_{\frac{1}{2}}$ (lux · sec) |
|---|---|
| II-24 | 4.9 |
| II-25 | 5.1 |
| II-26 | 5.4 |
| II-27 | 5.1 |
| II-28 | 5.7 |

TABLE IV-2-continued

| Compound No. | $E_{\frac{1}{2}}$ (lux · sec) |
|---|---|
| II-29 | 4.5 |
| II-30 | 4.9 |
| II-31 | 5.4 |
| II-32 | 4.8 |
| II-33 | 4.9 |
| II-34 | 4.5 |
| II-35 | 5.7 |
| II-36 | 5.1 |
| II-37 | 5.1 |
| II-38 | 5.6 |
| II-39 | 4.9 |
| II-40 | 4.9 |
| II-41 | 5.3 |
| II-42 | 5.1 |

As can be seen in Table IV-2, also the photosensitive materials with the hydrazone compounds Nos. II-24 to II-42 each as the charge transporting substance were found to be highly sensitive, giving good half decay exposure data.

EXAMPLE V-1

A coating liquid was prepared by kneading in a mixer 50 weight parts of 50 weight parts of metal-free phthalocyanine (available from Tokyo Kasei Kogyo) pulverized beforehand in a ball mill for 150 hours, 100 weight parts of the thiophene compound No. I-15 specified above, a polyester resin (Vylon; available from Toyobo Co., Ltd.) and the solvent tetrahydrofuran (THF) for 3 hours. A photosensitive layer was formed, in a dry thickness of 15 μm, on an aluminum-deposited polyester film (Al-PET) (electroconductive substrate) by applying the coating liquid to the substrate by the wire bar technique. Thus was prepared a photosensitive material.

EXAMPLE V-2

First, α-form metal-free phthalocyanine (starting material) was micropulverized in a LIMMAC (linear induction motor mixing and crushing) apparatus (Fuji Electric Co., Ltd.), where the α-form metal-free phthalocyanine was crushed in a nonmagnetic can containing Teflon pieces as working bodies, with said can disposed between two opposing linear motors, for 20 minutes. One weight part of the thus-micropulverized samples was dispersed in 50 weight parts of the solvent DMF (N,N-dimethylformamide) by ultrasonic treatment. The metal-free phthalocyanine sample was separated from the solvent by filtration and dried.

Then, a coating solution was prepared by mixing a solution of 100 weight parts of the thiophene compound No. I-15 mentioned above in 700 weight parts of tetrahydrofuran (THF) and a solution of 100 weight parts of polymethyl methacrylate polymer (PMMA; available from Tokyo Kasei Kogyo) in 700 weight parts of toluene. A charge transport layer was formed, in a dry thickness of 15 μm, on an aluminum-deposited polyester film substrate by applying the coating solution to said substrate using a wire bar. On the thus-obtained charge transport layer, there was formed a charge generating layer in a dry thickness of 1 μm by applying, with a wire bar, a coating liquid prepared by kneading in a mixer 50 weight parts of the metal-free phthalocyanine treated in the above manner, 50 weight parts of a polyester resin (Vylon 200; available from Toyobo Co., Ltd.), and the solvent THF for 3 hours. After drying, there was obtained a photosensitive material.

EXAMPLE V-3

A photosensitive material was prepared by forming a photosensitive layer in the same manner as in Example V-1 except that the composition of the charge generating layer was as follows: 50 weight parts of metal-free phthalocyanine, 100 weight parts of the thiophene compound No. I-15, 50 weight parts of a polyester resin (Vylon 200; Toyobo Co., Ltd.) and 50 weight parts of PMMA.

EXAMPLE V-4

A photosensitive material was prepared by forming a photosensitive layer in the same manner as in Example V-3 except that Chlorodiane Blue, a bisazo pigment, was used in lieu of metal-free phthalocyanine.

The thus-obtained photosensitive materials were measured for their electrophotographic characteristics using an electrostatic recording paper testing apparatus (Kawaguchi Denki model SP-428) according to the procedure of Example I-4. The results of the measurements are shown in Table V-1.

TABLE V-1

| Example | White light | | | Light of wavelength 780 nm | | |
|---|---|---|---|---|---|---|
| | $V_s$ Volts | $V_r$ Volts | $E_{\frac{1}{2}}$ Lux·sec | $V_s$ Volts | $V_r$ Volts | $E_{\frac{1}{2}}$ µJ/cm² |
| V-1 | 600 | 60 | 4.2 | 630 | 60 | 4.3 |
| V-2 | 650 | 70 | 3.5 | 700 | 80 | 3.9 |
| V-3 | 700 | 60 | 4.5 | 650 | 50 | 4.1 |
| V-4 | 730 | 70 | 3.8 | — | — | — |

As can be seen in Table V-1, the photosensitive materials of Examples V-1, V-2, V-3 and V-4 were comparable to one another with respect to half decay exposure amount and residual potential and were good also with respect to surface potential.

EXAMPLE V-5

A charge generating layer was formed on an aluminum plate having a thickness of 500 µm by vacuum vapor deposition of selenium to a thickness of 1.5 µm. Thereon was then formed a charge transport layer by applying, with a wire bar, a coating solution prepared by mixing a solution of 100 weight parts of the thiophene compound No. I-16 in 700 weight parts of tetrahydrofuran (THF) and a solution of 100 weight parts of polymethyl methacrylate (PMMA; Tokyo Kasei Kogyo) in 700 weight parts of toluene to give a dry layer thickness of 20 µm. When subjected to −6.0 kV corona discharge for 0.2 second, the photosensitive material obtained gave good results as follows: $V_s = -700$ V, $V_r = -100$ V, and $E_{\frac{1}{2}} = 5.1$ lux·sec.

EXAMPLE V-6

A coating liquid was prepared by kneading in a mixer 50 weight parts of metal-free phthalocyanine treated in the same manner as in Example V-1, 50 weight parts of a polyester resin (Vylon 200, Toyobo Co., Ltd.), and the solvent THF. A charge generating layer was formed, in a dry thickness of about 1 µm, on an aluminum support by applying the coating liquid to said support. Then, a charge transport layer, about 15 µm in thickness, was formed by applying a mixture of 100 weight parts of the thiophene compound No. I-17, 100 weight parts of a polycarbonate resin (Panlite L-1250), 0.1 weight part of a silicone oil, 700 weight parts of THF and 700 weight parts of toluene onto the charge generating layer.

When subjected to −6.0 kV corona discharge for 0.2 second in the same manner as in Example V-4, the photosensitive material obtained gave good results as follows: $V_s = -850$ V, $E_{\frac{1}{2}} = 5.0$ lux·sec.

EXAMPLE V-7

Photosensitive materials were prepared in the same manner as in Example V-4 except that the thiophene compounds Nos. I-18 to I-28 specifically shown hereinabove were used in lieu of the thiophene compound No. I-15.

The photosensitive materials were subjected to +6.0 kV corona dishcarge in the dark for 10 seconds and then illuminated with white light at an illuminance of 2 lux. The half decay exposure data ($E_{\frac{1}{2}}$) thus obtained are shown in Table V-2.

TABLE IV-2

| Compound No. | $E_{\frac{1}{2}}$ (lux · sec) |
|---|---|
| I-18 | 3.8 |
| I-19 | 4.5 |
| I-20 | 4.2 |
| I-21 | 5.3 |
| I-22 | 4.8 |
| I-23 | 4.2 |
| I-24 | 5.3 |
| I-25 | 5.2 |
| I-26 | 6.0 |
| I-27 | 4.1 |
| I-28 | 3.8 |

As can be seen in Table V-2, also the photosensitive materials with the thiophene compounds Nos. I-18 to I-28 each as the charge transporting substance were found to be highly sensitive, giving good half decay exposure data.

As mentioned hereinabove, the use, in accordance with the invention, of the above-mentioned thiophene compounds of general formulas (I) and (II) results in photosensitive materials having high sensitivity in the positive as well as in the negative charge mode of use and having excellent repeated-use characteristics. The charge generating substance can be selected so that it can fit to the exposure light source to be used. Thus, for instance, it is possible to obtain photosensitive materials usable in semiconductor laser printers by using phthalocyanine and/or a certain kind of bisazo compound. The durability of said materials can be improved by providing a covering layer on the surface thereof.

While the invention has been described in detail and with reference to specific embodiments thereof, it will be apparent to one skilled in the art that various changes and modifications can be made therein without departing from the spirit and scope thereof.

What is claimed is:

1. An electrophotographic photosensitive material comprising a photosensitive layer containing at least one thiophene compound selected from the group consisting of compounds having the general formulae (I) and (II):

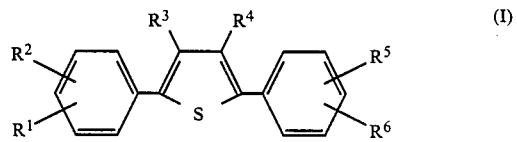

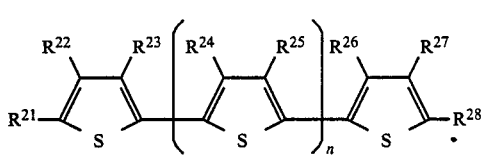

(II)

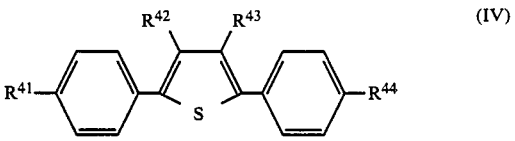

(IV)

wherein $R^1$, $R^2$, $R^3$, $R^4$, $R^5$ and $R^6$, and $R^{21}$, $R^{22}$, $R^{23}$, $R^{24}$, $R^{25}$, $R^{26}$, $R^{27}$ and $R^{28}$ each represents a hydrogen or halogen atom or a hydroxy group, an alkyl group, a hydroxyalkyl group, an alkoxy group, an allyl group, a vinyl group, an acyl group, a formylalkyl group, an acyloxy group, an alkoxycarbonyl group, an aryl group, a cyano group, a nitro group, an amino group, an alkylamino group or an arylamino group and n is an integer of 1, 2, 3, 4 or 5.

2. A electrophotographic photosensitive material as claimed in claim 1, wherein in $R^1$ to $R^6$ and $R^{21}$ to $R^{28}$ of the formula (I) and (II), the hydroxyalkyl group has from 1 to 10 carbon atoms, the alkyl group has from 1 to 10 carbon atoms, the alkoxy group has from 1 to 10 carbon atoms, and the acyl group represented by $R^1$ has from 1 to 10 carbon atoms, the formylalkyl group has from 2 to 10 carbon atoms, the acyloxy group has from 1 to 10 carbon atoms, the alkoxycarbonyl group has from 2 to 10 carbon atoms; the aryl group has from 6 to 18 carbon atoms, the alkylamino group represented by $R^6$ to $R^{18}$ has from 1 to 10 carbon atoms in the alkyl moiety thereof and the arylamino group has from 6 to 12 carbon atoms in the aryl moiety thereof.

3. An electrophotographic photosensitive material comprising a photosensitive layer containing at least one thiophene compound of the general formula (III):

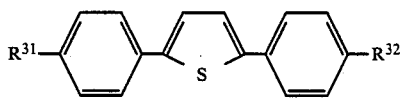

(III)

wherein $R_{31}$ and $R_{32}$ each independently is a hydrogen or a halogen atom or an alkyl group, an alkoxy group, a nitro group or an amino group.

4. An electrophotographic photosensitive material comprising a photosensitive layer containing at least one thiophene compound of the general formula IV:

wherein $R_{41}$, $R_{42}$, $R^{43}$ and $R^{44}$ each represents a hydrogen atom, a halogen atom, an alkyl group, an alkoxy group, an allyl group, a nitro group or an amino group.

5. An electrophotographic material for electrophotography comprising a photosensitive layer containing at least one thiophene compound of the general formula (V):

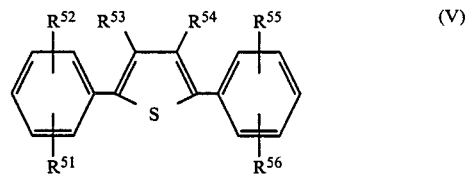

(V)

wherein $R_{51}$ to $R_{56}$ each represents a hydrogen or halogen atom or a hydroxy group, a hydroxyalkyl group, an alkyl group, an alkoxy group, an allyl group, a vinyl group, an acyl group, a formylalkyl group, an acyloxy group, an alkoxycabonyl group, an aryl group, a cyano group, a nitro group, an amino group, an alkylamino group or an arylamino group.

6. An electrophotographic photosensitive material as claimed in claim 1, wherein the photosensitive layer consists of a single layer containing both the charge generating substance and at least one hydrazone compound selected from the group consisting of the compounds represented by the formulae (I) and (II) claimed in claim 1.

7. An electrophotographic photosensitive material as claimed in claim 1, wherein the photosensitive layer consists of the combination of a charge generating layer containing the charge generating substance and a charge transporting layer containing at least one hydrazone compound selected from the group consisting of the compounds represented by the formulae (I) and (II) claimed in claim 1.

8. An electrophotographic photosensitive material as claimed in claim 6, wherein the proportion of the hydrazone compound claimed in claim 1 in the photosensitive layer is contained in an amount of 10 to 60 wt% with respect to the binder, and further wherein the proportion of the charge generating substance in the photosensitive layer is 10 to 60 wt% with respect to the binder.

9. An electrophotographic photosensitive material as claimed in claim 7, wherein the proportion of the hydrazone compound claimed in claim 1 in the charge transporting layer is 20 to 80 wt% with respect to the charge transporting layer.

* * * * *